(12) United States Patent
Freund (10) Patent No.: US 8,409,279 B2
(45) Date of Patent: Apr. 2, 2013

(54) BREAST IMPLANT IMPLANTATION METHOD AND APPARATUS

(75) Inventor: Robert M. Freund, Old Westbury, NY (US)

(73) Assignee: Lipose Corporation, Greenwich, CT (US)

( * ) Notice: Subject to any disclaimer, the term of this patent is extended or adjusted under 35 U.S.C. 154(b) by 54 days.

(21) Appl. No.: 12/773,310

(22) Filed: May 4, 2010

(65) Prior Publication Data

US 2011/0082546 A1     Apr. 7, 2011

Related U.S. Application Data

(60) Provisional application No. 61/247,697, filed on Oct. 1, 2009.

(51) Int. Cl.
*A61F 2/12*     (2006.01)

(52) U.S. Cl. ............................. 623/8; 383/38

(58) Field of Classification Search .................... 383/38, 383/40; 424/424; 623/8
See application file for complete search history.

(56) References Cited

U.S. PATENT DOCUMENTS

| 6,843,251 | B1 * | 1/2005 | Huerland et al. ............. 128/845 |
| 7,935,089 | B2 * | 5/2011 | Tsao .............................. 604/239 |
| 2008/0241212 | A1 | 10/2008 | Moses et al. |
| 2009/0204107 | A1 * | 8/2009 | Keller et al. ....................... 606/1 |

FOREIGN PATENT DOCUMENTS

| EP | 0727232 A2 | 8/1996 |
| EP | 0784987 A2 | 7/1997 |
| EP | 0895785 A2 | 2/1999 |

OTHER PUBLICATIONS

Int'l Search Report/Written Opinion issued on Feb. 2, 2011 in Int'l Application No. PCT/US2010/050696.
Int'l Preliminary Report on Patentability issued Apr. 12, 2012 in Int'l Application No. PCT/US2010/050696.
Office Action issued Jan. 18, 2012 in U.S. Appl. No. 12/773,281.

* cited by examiner

*Primary Examiner* — Bruce E Snow
(74) *Attorney, Agent, or Firm* — Panitch Schwarze Belisario & Nadel LLP (57) ABSTRACT

A method for implanting a breast implant into a subject, the method includes: providing a sterile, flexible, elastic biodegradable bag sized to contain the breast implant; providing a sterile breast implant; inserting, using sterile handling, the sterile breast implant into the sterile bag to form a sterile breast implant assembly; closing the bag to fully enclose the implant within the bag; and implanting in a sterile manner the sterile breast implant assembly into the subject. A sterile bag, which may be provided in a kit, preferably for use with the method includes first and second chambers connected by a channel for moving a breast implant from the first chamber through the channel to the second chamber without directly touching the implant. An incision dilator may also be included with the kit or separately provided for use in a preferred embodiment of the method.

16 Claims, 6 Drawing Sheets

BREAST IMPLANT IMPLANTATION METHOD AND APPARATUS

CROSS-REFERENCE TO RELATED APPLICATION

This application claims the benefit under 35 U.S.C. §119(e) to U.S. Provisional Patent Application No. 61/247,697, filed Oct. 1, 2009, the entire disclosure of which, in its entirety, is hereby incorporated by reference herein.

BACKGROUND OF THE INVENTION

The present invention relates to a breast implant implantation method and apparatus used in the method.

More particularly, one aspect of the present invention relates to a method for implanting a breast implant into a subject, the method comprising: providing a sterile, flexible, elastic biodegradable bag sized to contain the breast implant; providing a sterile breast implant; inserting, using sterile handling, the sterile breast implant into the sterile bag to form a sterile breast implant assembly; closing the bag to fully enclose the implant within the bag; and implanting in a sterile manner the sterile breast implant assembly into the subject.

Another aspect of the invention relates to a sterile bag, which may be provided in a kit, and preferably is used with one embodiment of the method. The bag includes first and second chambers connected by a channel for moving a breast implant from the first chamber through the channel to the second chamber without directly touching the implant. An incision dilator may also be included with the kit or provided separately for use in a preferred embodiment of the method.

Preferably the bag is made of a sterile, drug-eluting biodegradable material that preferably contains at least one drug for reducing or preventing infection, inflammation, capsular contracture, scarring or other indication or complication associated with breast augmentation or breast reconstruction.

Breast enhancement is commonplace in society. More than 600,000 breast augmentation procedures are performed in the U.S each year. Common problems involving breast implants include implant infection and capsular contracture, among other things.

Another issue arising with the use of breast implants is the formation of excess scar tissue around an implant. Such tissue can harden and lead to tightening around or squeezing of the implant, a phenomenon known as capsular contracture. While scar tissue and capsule formation is a normal process, when scar tissue is excessive the subsequent capsule is called capsular contracture and can lead to an implant that is misshapen, painful, hard and can attain an unnatural appearance and feel. Additionally, capsular contracture appears to be more common following infection, hematoma and seroma.

The reasons for implant infection in the early post-operative period can include residual blood following surgery, direct contact with breast ducts (that have bacteria within their lumens) that have been injured during surgery or other surgical contaminants. Current treatment includes antibiotic washings of the surgical site and implants at the time of surgery and oral antibiotics after surgery.

Infection can occur anytime from several days to several years after implantation; however, it occurs more frequently in the immediate post-operative period. Acute infection is diagnosed when the patient exhibits pain, fever, and tenderness around the implant usually manifested within several days from the time of surgery.

The reason for capsular contracture is not well-defined. However, several different treatments have yielded improved results with less chance of capsular formation. First, leukotriene receptor antagonists, such as zafirlukast (Accolate®), montelukast (Singulair®), and pranlukast administered orally have demonstrated the ability to moderate the capsular contracture. Second, antibiotics surrounding the implant have anecdotally been a source of improvement in capsular contracture. Finally, textured implants have yielded a reduction in capsule formation, but are not desirable because of aesthetic issues.

Implant infection is most commonly attributed to contamination of the sterile field during surgery or to contamination arising from lymph node or mammary duct dissection during surgery. Bacteria can migrate deep within the breast tissue via the mammary ducts. Incision through the ducts during subglandular placement thus opens a temporary but direct external route for contamination of the implant after placement. Bacteria colonized from the mammary ducts and nipples is similar to exogenous flora found on the skin, namely coagulase negative *Staphylococcus, P. acne*, and *Bacillus subtillus*.

Subclinical infection is perceived to be a contributor to capsular contracture. Subclinical infection is defined as bacterial colonization of a surface with or without biofilm formation. It does not produce the signs and symptoms traditionally associated with frank infection (such as pain, tenderness, fever, and pus) and manifests itself as a chronic inflammatory response. This inflammatory response leads to an overaggressive collagen deposition during tissue remodeling resulting in fibrous tissue buildup and capsule rigidity with eventual implant distortion.

Most surgeons engage in prophylactic efforts to reduce the incidence of infection associated with breast implants, including a no-touch technique by the surgeon. For example, in addition to meticulous attention to sterility, many surgeons irrigate the implant pocket and bathe the implant itself with gentamycin, cefazolin, povidone-iodine or another antibiotic solution. Post-operative counseling includes instructing the patient to neither touch the incision sites nor to immerse them in hot water for at least two weeks (or until healing is complete). Prophylactic oral antibiotics can also be given to patients prior to, during and after surgery to prevent post-implant colonization. Additionally, implant placement below the muscle avoids (or at least minimizes) surgical contact with the mammary ducts.

The present invention aids in the practice of no touch breast augmentation or reconstruction procedures by encasing the sterile implant in a sterile, biodegradable bag from which it does not have to be removed, such that the implant is not directly touched, but rather is implanted into the subject while encased in the bag, preferably made of a material containing at least one drug, such as one or more antibiotics or drugs useful in reducing or preventing infection and capsular contracture.

Adams and colleagues used a method for reducing capsular contracture caused by bacterial implant colonization. They provided an antibacterial irrigation solution and employed sterile technique prior to and during surgery. Adams' "triple antibiotic solution" originally contained a mixture of bacitracin, gentamycin, and cefazolin and was shown to be active against bacteria most commonly known to colonize breast implants. Adams subsequently published results of a six-year clinical study showing that patients who received surgeries incorporating these techniques have a 1% capsular contracture rate as opposed to national rates, which approached 15-20% in that same time period (Adams et al. (2006) Plast. Reconstr. Surg. 117:30-36).

Texturing the outside silicone surface has been employed as a technique to prevent capsular contracture. The textured surface causes a disorganization of collagen during deposition which minimizes capsule contracture. However, these implants have not significantly penetrated the market because, in use, tissue adherence to the textured surface leads to visible dimpling effect when the recipient moves. Textured implants also tend to have thicker shells than smooth implants and higher rupture rates.

The partial or total adhesion of the implant to the capsule due to such tissue ingrowth may be undesirable in the event it becomes necessary to remove or replace the implant. Notwithstanding the foregoing disadvantages, textured implants having a biocompatible, non-bioabsorbable outer tissue-contacting surface are generally considered to reduce the incidence of capsular contracture in patients.

There remains a need for an implantable filled breast prosthesis, referred to herein as a "breast implant," typically filled with silicone gel or saline solution, with or without gas pockets, that resists infection and capsular contracture following implantation and that resists adherence of the implant to the capsule.

The sterile, biodegradable bag of the present invention, when used with breast implants, and the method of the present invention, overcome these drawbacks while reducing or preventing capsular contracture as well as treating or preventing infection, pain, inflammation, scarring or other indications or complications associated with breast augmentation or breast reconstruction.

As used herein, the singular forms "a", "an", and "the" include plural referents, and plural forms include the singular referent unless the context clearly dictates otherwise.

Certain terminology is used in the following description for convenience only and is not limiting. Words designating direction such as "bottom," "top," "front," "back," "left," "right" and "sides" designate directions in the drawings to which reference is made, but are not limiting with respect to the orientation in which the bags, implant assemblies including bags or kits including them may be used. The terminology includes the words specifically mentioned above, derivatives thereof and words of similar import.

BRIEF SUMMARY OF THE INVENTION

One aspect of the present invention relates to a method for implanting a breast implant into a subject, the method comprising: providing a sterile, flexible, elastic biodegradable bag sized to contain the breast implant; providing a sterile breast implant; inserting, using sterile handling, the sterile breast implant into the sterile bag to form a sterile breast implant assembly; closing the bag to fully enclose the implant within the bag; and implanting in a sterile manner the sterile breast implant assembly into the subject.

Another aspect of the present invention relates to a bag for retaining and sterile handling of a breast implant, the bag comprising first and second chambers each having a volume when expanded larger than the implant, the first chamber having a closable opening for insertion of the implant, the bag further having a channel connecting the chambers where the channel has a diameter smaller than either chamber but large enough to accommodate the implant when the implant is elastically deformed without damaging the implant such that the implant may be manually moved without directly touching the implant from the first chamber through the channel and into the second chamber without adversely affecting the implant.

Yet another aspect of the present invention relates to a kit for use in handling and implanting a breast implant in a sterile manner, the kit comprising a bag comprising first and second chambers each having a volume when expanded larger than the implant, the first chamber having a closable opening for insertion of the implant, the bag further having a channel connecting the chambers where the channel has a diameter smaller than either chamber but large enough to accommodate the implant when the implant is elastically deformed without damaging the implant such that the implant may be manually moved without directly touching the implant from the first chamber through the channel and into the second chamber without adversely affecting the implant, the bag being within openable sterile packaging. The kit may include the sterile breast implant as a separate component outside of the bag or as encased within the bag as a preformed breast implant assembly. The kit may also include a sterile insertion dilator.

The bag used in all embodiments of the present invention preferably comprises at least one biodegradable polymer layer dimensioned and shaped to encase the breast implant and contains at least one drug to at least minimize at least one of infection and capsular contraction.

After the implant is inserted into the bag it is closed and sealed, preferably after the implant is bathed in an antibiotic solution and inserted into the bag.

The bag can inhibit or reduce formation of scar tissue in and around the implant and/or inhibit or reduce capsular contracture in and around the implant in a subject. When drugs are present in the polymer matrix that forms the bag, such drugs can elute into the surrounding tissue to inhibit, prevent or treat any bacterial infection or colonization for antimicrobial agents. Preferably, the drug is at least one antibiotic. Other drugs will also beneficially affect scarring and capsular contracture formation by interfering with collagen formation. Such other drugs include leukotriene receptor antagonists or inhibitors and/or calcium channel blockers. Other drugs may be used to treat other anticipated conditions, based on the subject and the subject's circumstances.

For example, the bag containing appropriate antibiotics can provide protection against colonization by bacteria until a complete capsule can form to block the mammary ducts that blocks bacterial colonization. The bag completely surrounding the implant provides a sterile barrier around the implant that can both kill any contaminating bacteria from the surgical implantation itself as well as elute antimicrobial agents and/or other drugs after surgery to prevent bacterial migration to the implant during the healing process and to reduce and preferably eliminate capsular contracture.

All embodiments of the bag of the invention can comprise multiple layers, typically from one to five layers. In one embodiment, the bag can include an inner layer facing the breast implant shell optionally containing at least one drug, one or more central polymeric layers that can optionally contain at least one drug, and an outer polymeric layer that can have a smooth or textured outer surface and optionally contain at least one drug, so long as at least one of the layers, and preferably all of them contain at least one drug. The different layers can contain the same or different drugs which can elute at different times based on the dissolution rate of the layers containing them. The polymeric inner layer and any intermediate and outer layers of the bag can be made of the same or different biodegradable polymers.

Any of the bags of the invention should completely encase the breast implant.

The bag is made of a flexible, elastomeric, biodegradable polymer that is sterilized in any suitable manner prior to use and is handled and implanted in a sterile, no touch manner.

Another aspect of the invention is a breast implant assembly comprising a biodegradable bag of the invention containing a breast implant.

Yet another aspect of the invention relates to an incision dilator and its use in implanting the breast implant assembly containing the breast implant in the body of a subject receiving the implant.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE PREFERRED EMBODIMENTS

Figure 1:
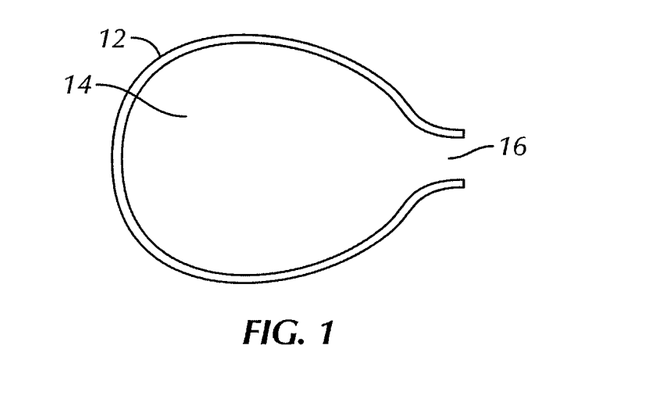
FIG. 1 is a vertical cross-sectional view of a first embodiment of a bag according to the present invention.
Figure 2:
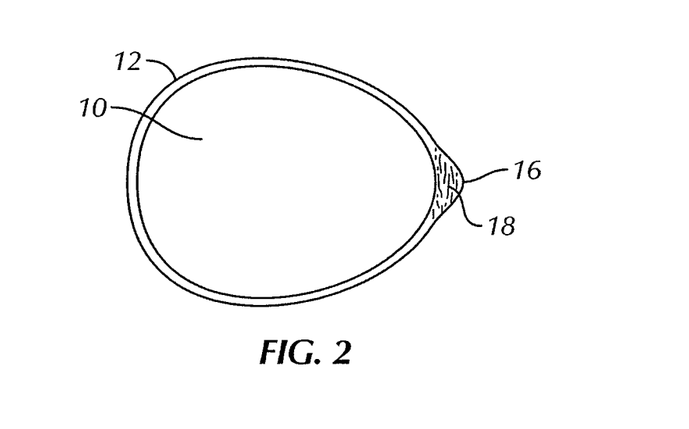
FIG. 2 is a vertical cross-sectional view of the bag of FIG. 1 containing a breast implant, where the bag has been closed and sealed after the implant has been inserted.

FIGS. 1 and 2 illustrate a first embodiment of a bag for use with the present invention for encasing a breast implant 10 to be implanted in a subject's body. As used herein, a "subject" typically refers to a human, and usually a woman, but also includes a man, where the implantation surgery and implantation generally uses standard breast reconstructive or augmentative surgical techniques, modified as described herein by the use of the bag containing the breast implant in a no touch procedure to assure sterility and reduce or prevent infection. However, the subject could also be any desired animal. Breast reconstruction usually occurs following complete mastectomy but can be also be done for a partial mastectomy usually in women, but also in men, as well as to correct or repair congenital deformities or traumatic injury to the breast. Breast augmentation is typically done by women for cosmetic reasons or by men regarding transgender surgery. A "no touch" procedure involves not touching the implant with any comtaminants, including without limitation surgical gloves, used surgical instruments, the skin surrounding the incision or the transected lacrimal ducts within the body. Nothing but the inside surface of the bag containing or to contain the implant should come into contact with the implant in a "no touch" procedure from the time the implant is removed from a sterile container until it is implanted into the subject. If and when gloves or implements contact any unsterile object in the operating theater, they are discarded or put aside for re-sterilization and new gloves and implements are used.

With reference to the embodiment of FIGS. 1 and 2, a bag 12 includes a single chamber 14 for receiving and retaining the implant 10 through an opening 16. The opening 16 may be in the form of a slit, or a wider opening where the material around the opening can readily be overlapped to fully cover the implant so as to minimize and preferably prevent infection to an uncovered portion of the implant. Those of skill in the art can readily determine appropriate shapes, sizes and configurations for the openings or slits for a given size and shape of breast implant. The bag 12 is made of a flexible, elastomeric, biodegradable material, preferably a biodegradable polymer, which dissolves in the subject's body. After the implant 10 is sterilized and inserted preferably using a no touch procedure, the bag is closed, typically with sterile, biodegradable sutures 18 applied using a sterile needle. Alternatively or additionally, the closure may be made and/or sealed using biodegradable glue, such as fibrin glue, or a hydrogel glue made by mixing aldehyded dextran and ε-poly(l-lysine), as described in M. Araki, et al., *J. Thorac. Cardiovasc. Surg.*, 2007; 134: 1241-1248 Any other biodegradable glue known to those in the art may also be used, if desired.

Once encased within the bag 12, the implant 10 does not come into contact with anything other than the interior of the bag, thus assuring sterility and reducing or eliminating infection and foreign body contamination, as well as reducing the opportunity for adverse damage or weakening of the implant by direct handling. The implant encased within the bag forms a breast implant assembly. The term "breast implant assembly" as used herein also includes a bag supplied separately for encasing the implant and delivered to or available in the operating room for surgery, where the implant is encased within the bag to form the breast implant assembly at the time of the surgery. The bag may also be preassembled with the breast implant and supplied for surgery as a prepackaged breast implant assembly.

As used herein, a material, such as a polymer, glue or sutures, is "biodegradable" when it is hydrolytically labile, oxidatively labile, or susceptible to enzymatic action, or any combination thereof, that leads to the degradation or absorption of the polymer or other material within the body of the subject in which it is implanted. Such materials are also biocompatible such that they are compatible with living tissue or a living system and is acceptable for use in or by animals or humans. Thus, a biocompatible material does not cause physiological harm to any significant or unacceptable degree, does not cause any or any significant amount of inflammation or immunological reaction, and is not toxic or injurious to the living tissue or system. For example, a biocompatible material can be ingested, implanted, placed on or otherwise used in a living subject or tissue without adverse effects. Biodegradable polymers and other materials have various times for degradation and dissolution, which can depend, for example, on the nature and size of the breakdown products.

The biodegradable polymer or other material used to form the bag 12 preferably contains at least one drug, such as one or more antibiotics or drugs useful in reducing or preventing infection and capsular contracture, where the drug or drugs preferably are eluted from the material as the material dissolves in the subject's body after implantation.

The bag 12 has an appropriate shape for the implant 10, and may be but need not be form-fitting to closely fit against the outer surface of the implant. Preferably, to ease insertion of the implant into the bag and the handling of the breast implant assembly including the bag and its encased implant, the bag 12 has a volume when expanded of about 5% to about 10% larger than the implant. The larger bag allows for easier insertion of the implant into the bag and greater ease of manipulating the implant within the bag without contaminating the implant or risking rupture of the bag.

The biodegradable bag has substantially the same shape as the implant 10 (e.g., round, teardrop, contoured, anatomical and the like), and completely encases the implant when the bag is closes and/or sealed. The bag can be manufactured in several different sizes to accommodate most typically sized and shaped breast implants. Thus, for example, the bag could be sized to accommodate small (about 120 mL to about 250 mL), medium (about 250 mL to about 400 mL), or large (about 400 mL to about 800 mL), and any other sized breast implants.

The biodegradable bag of the invention, especially one that preferably includes at least one drug, is useful to reduce capsular contracture and to deliver drugs into the surrounding tissue, to facilitate healing or to reduce and preferably prevent infection, pain, and/or other conditions, indications or complications associated with breast implants. In this preferred embodiment, the bag acts as a carrier of the drugs, and may be a repeating structure of amino acids, such as tyrosine, leucine or arginine, or other biodegradable polymeric materials, and more particularly, a fibrous composite of two submicrometer poly(ester urethane) urea (PEUU) and poly(lactide-co-glycolide) (PLGA) fibers, described in more detail below.

Any of the embodiments of bag the invention, including for example the bag 12 described above or a bag 20 of the second embodiment described below, or any other bag according to the present invention, can be a single layer or multiple layers of any suitable thickness, and preferably has a substantially uniform thickness, except where a textured layer or layers are desired. For the bag 12 of the first embodiment of the invention, a smooth outer surface is desired to enhance ease of implantation within an incision during the implantation procedure. Other embodiments of bags may also have smooth surfaces or have at least a portion with at least one textured or crinkled surface, if desired.

Certain physicomechanical properties of the bag of the invention are similar to those of the implant shell. For example, at body temperature, both the shell and the bag are soft and malleable. Usually, however, the bags of the invention are thinner than the implant shell, so as to be on the order of about 1 mil (about 0.0254 mm) to about 10 mils (about 0.254 mm), typically on the order of about 1.15 mils (about 0.0292 mm) to about 3 mils (about 0.0762 mm). The bag is also elastomeric so that it can expand to accommodate the implant readily, but not so elastomeric that pressing on one portion of the bag does not move the implant within the bag, important as described below with respect to the second embodiment of the bag 20. The bag can be made entirely of a fibrous, knit, woven, or non-woven construction to impart softness and flexibility to readily encase the breast implant. The elasticity of the bag should be sufficient enough to expand the bag to three times its normal volume without loss of integrity or rupture.

The bag containing the drug or drugs to be eluted should be sufficiently thick to control the time of elution before the layer or layers forming the bag are dissolved within the subject receiving the implant in the bag of the invention. In multilayered embodiments, the layers, some of which may contain and therefore elute different drugs, typically are formed or applied serially one on the other. The thickness of a layer typically depends on viscosity, which in turn depends on polymer concentration in a solution used to make the covering. Thickness of the covering or coating can be increased by increasing the number of dips, sprays or other techniques used to make the covering.

Methods of preparing the single or multiple polymer layers for the bag of the invention include, for example, dip molding, spray coating, single stream or dual stream electrospinning which use nanofibers, and other methods which are conventional or known in the art. Materials for the molds for the bags are conventional, such as plastics like polypropylene, nylon, polytetrafluoroethylene, delrin; metals like stainless steel and titanium; or glass or ceramics. Those skilled in the art could readily obtain or fabricate molds or other equipment compatible with the polymer used to make the bag, which of course must be readily removable from the molds. The bags could also be extruded using typical extrusion equipment, operated at temperatures sufficient to melt extrude the bag without deactivating any active pharmaceutical ingredient or drug within the material used to make the bag.

Many biodegradable polymers are suitable for use in producing the bag of the invention. In selecting polymers for use in the invention, the glass transition temperature (Tg) of the polymers, as well as the polymer-drug combination can be considered along with other parameters. Polymers with high Tg tend to be stiff and if made into films, would be too stiff for use in the bag for the breast implants in such a form. In such cases, incorporation of drugs can lower glass transition temperatures, making the stiffer polymers softer and more suitable for use. Alternatively, these high Tg polymers remain useful for the invention since they can be nanospun into felts for formation into a bag of the invention. Such felts render the bag soft even if the polymer itself may be stiff when formed into a film. For example, polymers with sufficiently low Tg can be pressed into films at low temperatures. Since some drugs may decompose at high temperature, a low Tg polymer offers the ability to use thermal methods even in the presence of drugs. As used herein, low Tg polymers are those having a Tg below 40° C. The bag of the invention made from films, e.g., as are prepared by dip coating, desirably have a Tg of about 20° C. to about 30° C., but can vary from as low as about 10° C. up to about body temperature or even to about 40° C. These Tg values are for the final formulation of the bag (including polymer, drug or any other ingredient), as it is well known that adding excipients (e.g., drugs or plasticizers) to polymers can either lower or increase the Tg.

One way to assess whether a bag has sufficient flexibility for use in the invention is to measure the elongation of the polymer. Suitable films have an elongation at yield of about 10% to about 400%, such that films are generally too stiff if elongation is below 10% and too pliable if above 400%.

It is within the skill of the art to select polymers, drugs and processing methods to prepare the bag and to preferably incorporate at least one drug into the bag of the invention.

Exemplary biodegradable polymers suitable for use in forming the bags of the invention include but are not limited to:

polylactic acid, polyglycolic acid and copolymers and mixtures thereof, such as poly(L-lactide) (PLLA), poly(D,L-lactide) (PLA), polyglycolic acid or polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL);

poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol (PEG), polyalkylene oxides (PAO), hydroxypropylmethylcellulose, polysaccharides such as hyaluronic acid, chitosan and regenerate cellulose, and proteins such as gelatin and collagen, and mixtures and copolymers thereof, and polyester urethane urea (PEUU).

Other suitable biodegradable polymers and copolymers may also be used, as well as polyethylene glycol (PEG) derivatives or blends of any of the foregoing. All such polymers which provide the desired flexibility, pliability and/or softness to the bags are contemplated for use to make the bag of the invention.

In some embodiments, biodegradable polymers have diphenol monomer units that are copolymerized with an appropriate chemical moiety to form a polyarylate, a polycarbonate, a polyiminocarbonate, a polyphosphonate or other class of polymer.

For example, suitable biodegradable tyrosine-derived polyarylates include those described in U.S. Pat. Nos. 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337. These patents and publications also disclose other useful polymers containing tyrosine-derived diphenol monomer units or other diphenol monomer units, including polyarylates, polycarbonates, polyiminocarbonates, polythiocarbonates, polyphosphonates and polyethers.

Likewise, the foregoing patents and publications describe methods for making these polymers, some methods of which may be applicable to synthesizing other biodegradable polymers. The foregoing patents and publications also describe blends and copolymers with polyalkylene oxides, including PEG. All such polymers are contemplated for use in the present invention.

The representative structures for the foregoing polymers are provided in the above-cited patents and publications which are incorporated herein by reference in their entireties. Polyarylates are among the preferred materials because their physical characteristics can match those of silicone. Additionally, polyarylates are preferred because their range of Tg can be manipulated to form a suitable bag for a breast implant.

Abbreviations used herein for naming polymers and the subunits thereof include B, 4-hydroxybenzoic acid; Bn or Bz, benzyl; D or DAT, desaminotyrosine or desaminotyrosyl; DATE, desaminotyrosine ethyl ester; E or Et, ethyl; glu, glutarate; M or Me, methyl; PEG, polyethylene glycol; Succ, succinate; and T, tyrosine.

As used herein, polymers based on diphenol monomer units have two-part names. The first part identifies the diphenol moiety and the second part identifies the group with which the diphenol moiety is copolymerized. The names are written in the form poly(diphenol diacid), poly(diphenol carbonate), poly(diphenol iminocarbonate), etc.

The diphenol moiety is generally named for its three components, the two aromatic ring moieties and the tyrosine ester moiety. For example, DTE is desaminotyrosyl-tyrosine ethyl ester; DTBn is desaminotyrosyl-tyrosine benzyl ester. When a free acid is present (rather than an ester), the name for a third component is omitted. Thus, DT is the corresponding free acid form, namely desaminotyrosyl-tyrosine. BTE is the diphenol monomer 4-hydroxy benzoic acid-tyrosine ethyl ester; BT is the corresponding free acid form, namely 4-hydroxy benzoic acid-tyrosine.

The second part of the name identifies the group with which the diphenol moiety is polymerized, such as the diacid, the carbonate, the iminocarbonate and the like. Hence, specific examples include poly(DTE glutarate), poly(DTBn carbonate) and the like.

If a mixture of diphenol moieties or of copolymerized groups (such as two diacids) are present in the polymer, then that part of name may includes the designation "co" or may have a hyphen, along with an indication of percentage of one of the two moieties. For example, poly(DTE:10DT-co-succinate) and poly(DTE-10-DT succinate) are used interchangeably to mean a polymer made by copolymerizing a mixture of 90% desaminotyrosyl-tyrosine ethyl ester and 10% desaminotyrosyl-tyrosine with the diacid succinic acid. An example of a mixed diacid is poly(DTE-co-50:50 PEG-bis-succinate adipate).

Additional preferred polyarylates are random copolymer of desaminotyrosyl-tyrosine (DT) and an desaminotyrosyl-tyrosine ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can optionally have a polyalkylene oxide therein. Similarly, another group of polyarylates are similar to the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used in forming the polyarylates) include succinic, glutaric, sebacic, adipic and glycolic acid as well as PEG or other PAOs and polyethylene glycol diacids such as the polyethylene glycol-bis-alkyl diacids described in U.S. Pat. No. 7,271,234.

Useful tyrosine-derived polyarylates are the DTE-DT succinate family of polymers, e.g., those polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT.

Some polyarylates have inherent microtexturing, which may be desirable in forming a temporarily-textured outer surface on the bag 20 or other embodiments besides the bag 12 of the first embodiment, which is preferred to have a smooth outer surface.

One exemplary, presently preferred biodegradable material for making all embodiments of the bag of the invention is an elastic biodegradable polymer made from a fibrous composite sheet with two distinct submicrometer fiber populations, namely biodegradable poly(ester urethane) urea (PEUU) and poly(lactide-co-glycolide) (PLGA), where the PLGA can be loaded with at least one drug, such as the antibiotic tetracycline hydrochloride (PLGA-tet). A two-stream electrospinning setup was developed to create a uniform blend of PEUU and PLGA-tet fibers. Composite sheets were flexible with breaking strains exceeding 200%, tensile strengths of 5-7 MPa, and high suture retention capacity. The blending of PEUU fibers markedly reduced the shrinkage ratio observed for PLGA-tet sheets in buffer from 50% to 15%, while imparting elastomeric properties to the composites. The formation of this material and its properties using PLGA-tet are described in Y. Hong, et al., "Generating Elastic, Biodegradable Polyurethane/Poly(lactide-co-glycolide) Fibrous Sheets with Controlled Antibiotic Release via Two-Stream Electrospinning," *Biomacromolecules*, 2008, 9, No. 4, 1200-1207, the entire disclosure of which is hereby incorporated herein by reference. Other antibiotics besides or in addition to tetracycline, or other drugs and combinations thereof may be incorporated into this material and used to form the bag of the present invention.

Any drug, biological agent, or active ingredient that is compatible with the process of preparing the bag of the invention can be incorporated into one or more of the polymeric biodegradable layers.

Doses of such drugs and agents are known in the art. Those of skill in the art can readily determine the amount of drug or agent desired for delivery, and calculate the amount of that should be loaded into the polymeric layer or layers of the bag for encasing a breast implant of a particular volume.

The drug or drugs are retained in the bag and in essence provide for a topical application of the drug or drugs. The active agents may be a mixture of leukotriene antagonist, antibiotic and calcium channel blocker that is released to the surface of the breast implant and the body cavity in which the implant is implanted. The drug or drugs mixture can be applied in a time-release fashion by blending the drug or drug mixture into the material used to make the biodegradable polymer, typically when the materials of the polymer are in a solution, suspension or other liquid form, or by otherwise incorporating them into the biodegradable polymer at any stage of its preparation or manufacture, in a fashion that allows for controlled release preferably from about one day to about 18 months. The biodegradable polymer will release the drug or mixture of drugs and then dissolve away.

Drug elution times can be determined based on the drug and its time course of action, which generally and more preferably are over the course of about 3 days to about 100 days. For example, antibiotic activity for 7-10 days (or more) can be sufficient to prevent or reduce colonization of implants, thereby preventing or reducing capsular contracture (or its overall incidence as could be assessed, for example, in a clinical trial).

In accordance with the invention, the drugs and biologically-active agents for formulation into the polymeric layer or layers of the bag include, but are not limited to, antibiotics, anti-inflammatory agents, fibrosis-inhibiting agents, anti-scarring agents, leukotriene inhibitors or antagonists, cell growth inhibitors, calcium channel blockers, or other agents effective to treat various conditions associated with implant surgery and recovery.

As used herein, the terms "drug" and "drugs" are used to include all types of therapeutic agents, whether small molecules or large molecules such as proteins, nucleic acids and the like. The drugs of the invention can be used alone or in combination.

Certain preferred agents include antibiotics; leukotriene antagonists, such as zafirlukast (Accolate®), montelukast (Singulair®), pranlukast and zileuton; antineoplastic agents, such as 5-fluoruricil; nitric oxide producing agents, such as L-arginine; calcium-channel blockers, such as verapamil; TNF; interleukins; interferons; paclitaxel or other chemotherapy agents; 2-mercaptoethanesulfonate; antifungal agents; as well as any other agent, especially those that are known to for their ability to reduce capsular contracture.

Examples of non-steroidal anti-inflammatory agents include, but are not limited to, acetaminophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin and trolamine.

Examples of antimicrobial drugs include, but are not limited to:

aminoglycosides, such as amikacin, gentamicin, kanamycin, neomycin, streptomycin, and tobramycin;

antibiotics, such as bacitracin, clindamycin, daptomycin, lincomycin, linezolid, metronid, polymyxin, rifaximin, vancomycin;

cephalosporins, such as cephazolin or cephalexin;

macrolide antibiotics, such as erythromycin, azithromycin and the like;

β-lactam antibiotics, such as penicillins;

quinolones, such as ciprofloxacin;

sulfonamides, such as sulfadiazine;

tetracyclines, such as minocycline and tetracycline; and other antibiotics, such as rifampin, triclosan and chlorhexidine.

Other drugs, besides those discussed above, that can be incorporated into the biodegradable polymeric layer or layers of the bag of the invention, include, but are not limited to, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, nicotinic acid, chemodeoxycholic acid, chlorambucil and antineoplastic agents such as paclitaxel, sirolimus, 5-flurouracil and the like. Other drugs include those that act as angiogenensis inhibitors or inhibit various growth factors such as epidermal growth factor, PDGF, VEGF, FGF (fibroblast growth factor) and the like. These drugs include anti-growth factor antibodies (neutrophilin-1) and growth factor receptor-specific inhibitors such as endostatin.

As also mentioned above, any other drug or active therapeutic agent may be used, depending on the condition of the subject into which the implant is implanted, and particularly those that reduce, prevent or treat capsular contraction or other capsule formation can be incorporated into the bag of the invention.

Preferred antimicrobial agents of the invention include bacitracin, cephalexin and gentamicin, alone or in combination.

Examples of leukotriene inhibitors or leukotriene receptor antagonists include, but are not limited to, leukotriene receptor antagonists such as acitazanolast, iralukast, montelukast, pranlukast, verlukast, zafirlukast, and zileuton.

Once the drug or combination of drugs, and their appropriate concentration and dosage have been selected, the drug or drugs are mixed with the material used to form the one or more layers of the bag, which is provided in liquid form, typically in a solution with a biocompatible solvent appropriate for the particular biodegradable polymer or polymer precursor. The drug-polymer or polymer precursor composition is then applied either to an appropriately-shaped mandrel or mold to form a cover, or applied to the implant directly to form a bag, by any of the above-mentioned methods. The resulting product is then dried, typically with mild heating, to drive off the solvent. This produces the bag for separately encasing the implant with the drug elutably contained within the material used to make the bag. If multiple layers are desired, which may have the same or different concentrations of the same drug or drug combination or different drugs or drug combinations, the process is repeated for each layer. The inner or outer surface or both, of the bag may be textured, or portions thereof as desired, using a textured mandrel or mold, air or other gas spraying or the like.

Figure 8:
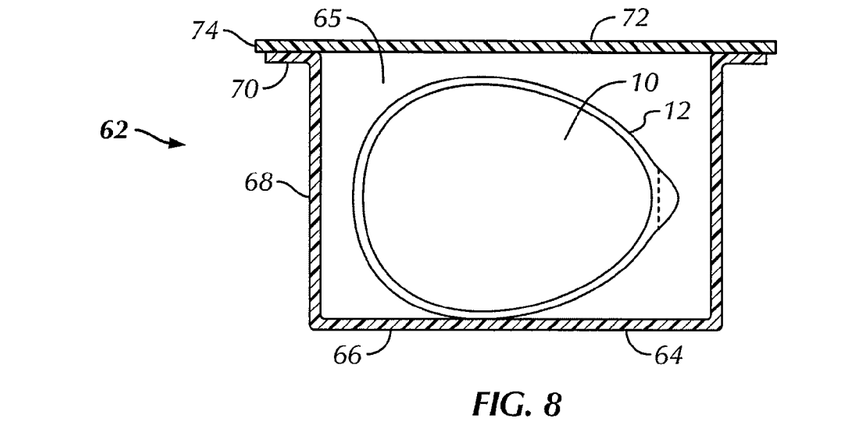
FIG. 8 is a vertical cross-sectional view of packaging for a kit according to one embodiment of the invention containing a breast implant in a bag as shown in FIG. 2.
Figure 9:
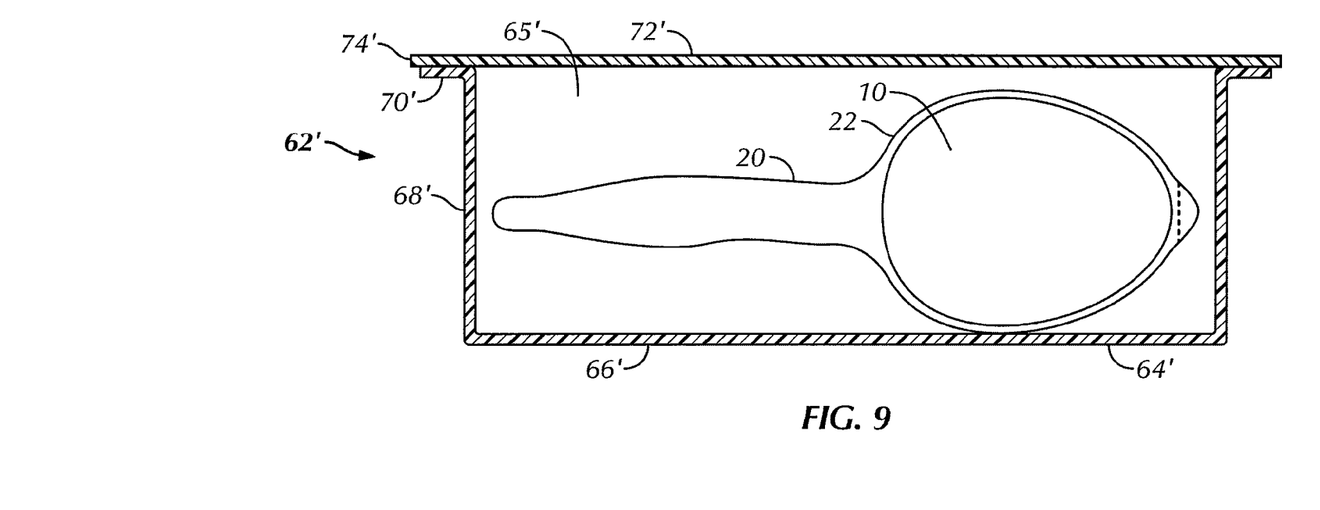
FIG. 9 is a vertical cross-sectional view of packaging for a kit according to another embodiment of the invention containing a breast implant in a bag as shown in FIG. 4.

After manufacture, the bag of the invention may be sterilized and packaged for assembly onto a breast implant immediately prior to surgery. Alternatively, the bag of the invention can be assembled to encase the breast implant, sterilized and packaged at the time of manufacture, so that a completed breast implant assembly is delivered to the surgical suite. Exemplary packaged breast implant assemblies are shown in FIGS. 8 and 9, described in more detail below. In any event, sterile gloves and sterile and atraumatic instruments should be used when handling the bags and implants to provide a sterile breast implant assembly of the implant within the bag.

Once the implant is retained within the bag, the implant assembly can be implanted into the subject as described below. As set forth above, the method generally includes: providing a sterile, flexible, elastic biodegradable bag sized to contain the breast implant; providing a sterile breast implant; inserting, using sterile handling, the sterile breast implant into the sterile bag to form a sterile breast implant assembly; closing the bag to fully enclose the implant within the bag; and implanting in a sterile manner the sterile breast implant assembly into the subject.

The invention will be described further with reference to FIGS. 3-13.

Figure 3:
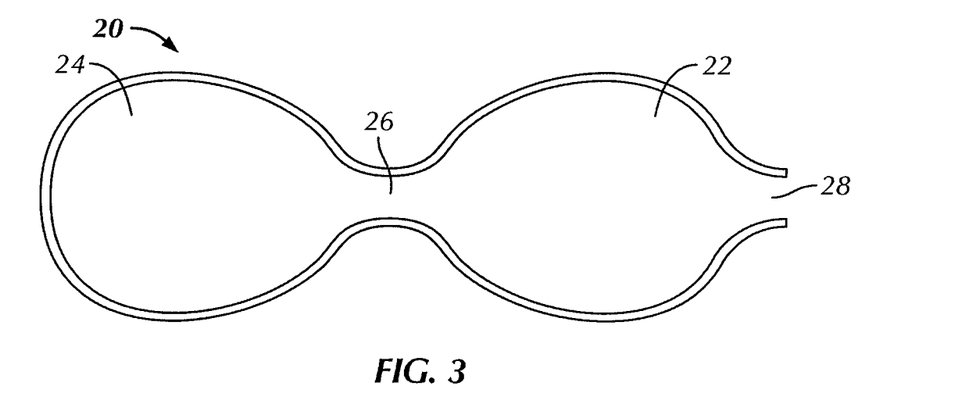
FIG. 3 is a vertical cross-sectional view of a second embodiment of a bag according to the present invention, where the bag is shown as having expanded first and second chambers connected by a channel for moving a breast implant from the first chamber through the channel to the second chamber without directly touching the implant.
Figure 4:
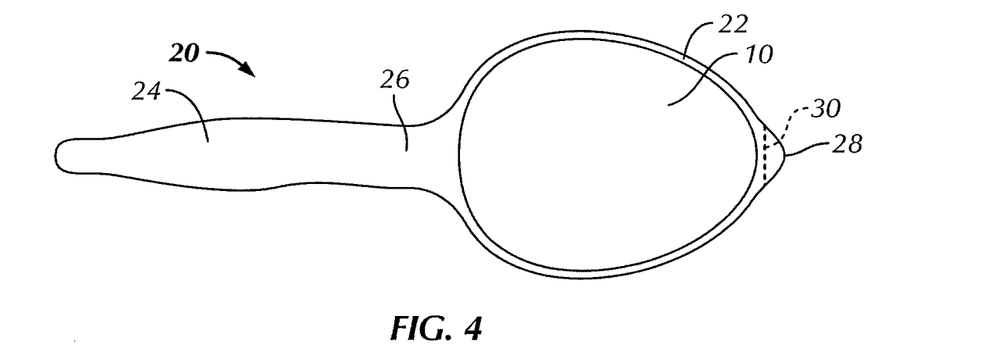
FIG. 4 is a vertical cross-sectional view of the bag of FIG. 3 containing a breast implant in the first chamber, where the bag has been closed and sealed after the implant has been inserted, and where the second chamber has not been expanded.
Figure 5:
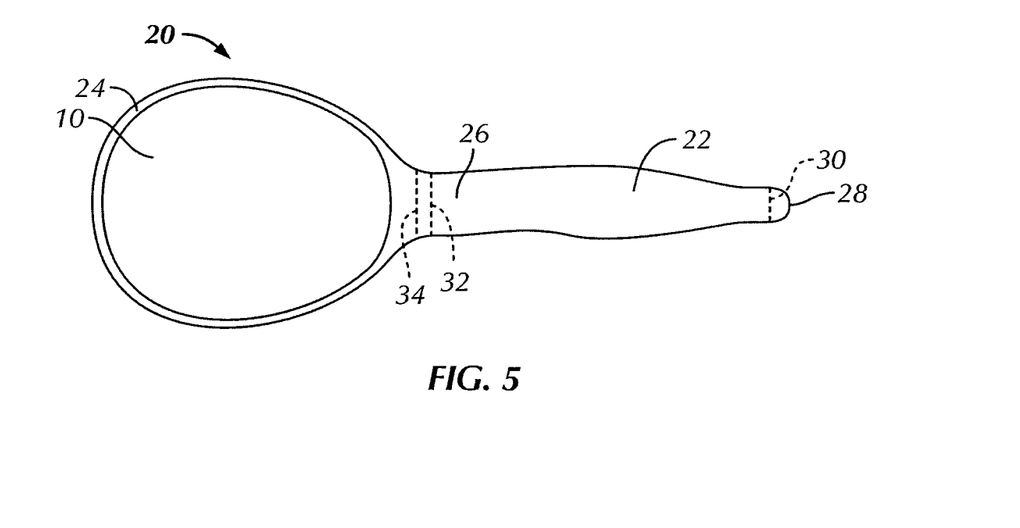
FIG. 5 is a vertical cross-sectional view of the bag of FIG. 4 after the breast implant has been moved from the first chamber through the channel to the second chamber, such that the first chamber is no longer expanded.

FIGS. 3-5 are vertical cross-sectional views of a second embodiment of a bag 20 according to the present invention. The bag 20 is shown in FIG. 3 as having and expanded first chamber 22 and an expanded second chamber 24 connected by a channel 26 for moving a breast implant from the first chamber 22 through the channel 26 to the second chamber 24 without requiring the surgeon or other medical personnel to directly touch the implant. Preferably, each of the first and second chambers has a volume when expanded of about 5% to about 10% larger than the implant, for the reasons explained above. Thus, regarding the bag 20, the channel 26 has a diameter that is smaller than either chamber 22 or 24, but that is large enough to accommodate the implant 10 when the implant is elastically deformed without damaging the implant, such that the implant may be manually moved without directly touching the implant from the first chamber 22 through the channel 26 and into the second chamber 24 without adversely affecting the implant 10. This is done in the method of the invention described below after the second chamber 24 and the channel 26 are inserted into an incision used to implant the implant assembly including a portion of the bag 20 into a desired implant location in the subject. If desired, at least the second chamber of the bag may have an outer surface that textured or crinkled. Otherwise the bag 20 may have an inner or outer surface that is smooth.

FIG. 4 shows the bag 20 containing a breast implant 10 in the first chamber 22, where the bag has been closed and preferably sealed after the implant has been inserted through an opening 28 leading to the first chamber 22, as described above regarding the first embodiment of FIGS. 1 and 2, using sterile biodegradable sutures and/or a sterile biodegradable glue. As shown in FIG. 4, the second chamber 24 has not been expanded yet, though it could be configured to have a greater initial collapsed or unexpanded volume than as shown based on the size of the implant to be contained therein, closer to the expanded size as shown in FIG. 3. At this stage of the implantation method of the invention using the bag 20, the second chamber 24 is not yet expanded or if expanded is collapsed to be inserted through an incision of a type described below in the subject, and preferably using an incision dilator 36, shown in FIGS. 6 and 7 as also described below.

FIG. 5 shows the bag 20 after the breast implant 10 has been moved from the first chamber 22 through the channel 26 to the second chamber 24, such that the first chamber is no longer expanded. This would be done after the second chamber 24 and channel 26 are inserted into the incision to place the implant 10 in the second chamber within the subject, but is shown in FIG. 5 outside of the subject for purposes of clarity. The implant 10 is moved by squeezing a portion of the first chamber 24 of the bag 20 containing the implant 10 to deform the implant without damage and to move the implant from the first chamber 22 into the channel 26, preferably within and through the incision dilator 36 described below, and then into the second chamber 24.

Once the implant 10 is in the second chamber 24 within the body of the subject, the second chamber 24 is closed to encase the implant 10 in the second chamber 24 within the subject's body. The second chamber 24 is closed as indicated by closure 34 in FIG. 5, and preferably sealed after the implant has been inserted into the second chamber 24 as described above regarding the first embodiment of FIGS. 1 and 2, using sterile biodegradable sutures and/or a sterile biodegradable glue.

Once the implant 10 is encased within the second chamber 24, the bag 24 is cut at the channel 26 in the vicinity of the connection of the channel 26 to the second chamber 24 distal (from the position in the subject) to the location where the second chamber 24 has been closed, as noted by the dashed lines 32 in FIG. 5. Thereafter, the portion of the channel 26 and the first chamber 22 that have been cut away from the second chamber 24 are removed for disposal. If desired, biodegradable glue also can be applied to the closure 34 after the excess portion of the bag 20 has been cut and removed.

While a breast implant assembly formed by the bag 12 of the first embodiment shown in FIG. 1 encasing the implant 10 as shown in FIG. 2 may be manipulated through an appropriate incision in the subject to the desired location, by directly pushing such a breast implant assembly through the incision, which may be dilated by appropriate surgical instruments as in a typical implantation procedure or by using the incision dilator of this invention described below, another technique or procedure is preferably performed using the second embodiment of the bag 20 and the implant 10 when the implant is in the first chamber 22 as shown in FIG. 4.

Starting with the breast implant assembly in the configuration of FIG. 4, the enhanced procedure includes using an incision dilator 36 of a type shown in FIGS. 6 and 7 where the procedure also is described below.

The incision dilator 36 includes a flexible, elastic portion 38 that may be made of any suitable flexible, elastic material capable of being sterilized, such as any of several types of synthetic elastomers, such as vinyl, latex, nitrile rubber or the like. Preferably, the elastomer is one that is most likely to be hypoallergenic to most people. The flexible, elastic portion 38 is to be inserted into the incision into the body of the subject for guiding the second chamber 24 and a connected portion of the channel 26 of the bag 20 of the breast implant assembly into a desired location within the subject's body. The flexible, elastic portion 38 is generally conical in shape as shown in FIG. 6, and has an expandable exit opening 40 at an exit end of the incision dilator 36 through which the unexpanded or collapsed second chamber 24 and portion of the channel 26 are inserted into the desired body location. The incision dilator 36 has a dilation portion 42 connected to the flexible, elastic portion 38, the dilator portion 42 being sufficiently non-flexible so as to be capable of dilating the incision. The dilator portion 42 extends into the incision sufficiently to dilate the incision and defines an entry opening 43 for initially receiving the unexpanded or collapsed second chamber 24 and at least a portion of the channel 26 before the second chamber 24 and channel 26 contain the implant 10.

Figure 6:
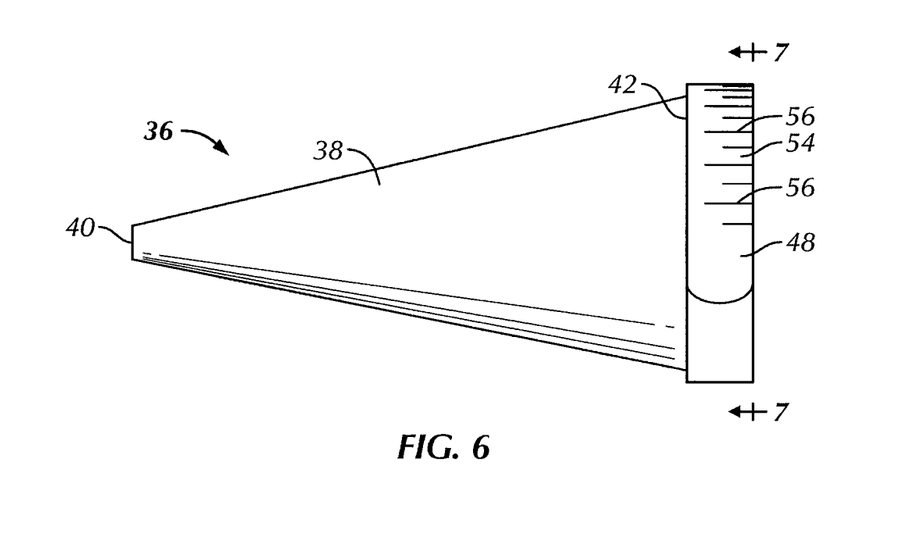
FIG. 6 is a side elevation view of an incision dilator for use in one embodiment of the breast implant implantation method of the present invention involving a breast implant assembly using the second embodiment of the bag of FIG. 3.
Figure 7:
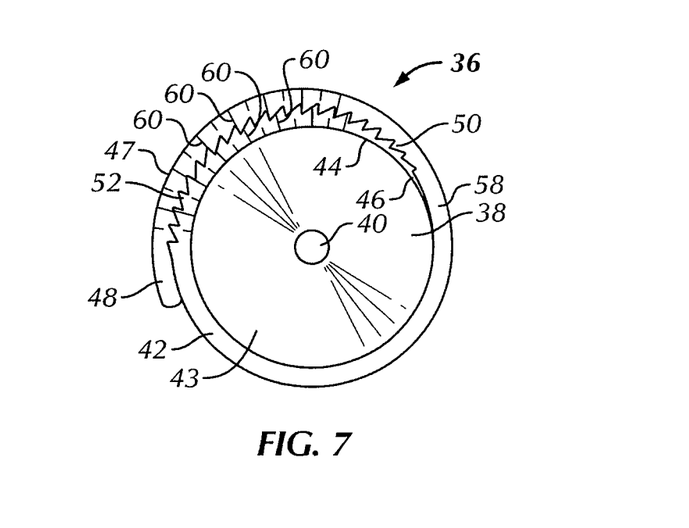
FIG. 7 is a front or entry end elevation view of the incision dilator of FIG. 6, taken along lines 7-7 of FIG. 6.

In one embodiment as shown in FIGS. 6 and 7, the dilator portion 42 may be in the form of a single strip of synthetic polymeric plastic, such as nylon, delrin, polypropylene, or metal such as spring stainless steel, or any other material that has sufficient stiffness to dilate an incision yet sufficient flexibility to be able to expand and contract in diameter as explained below. In the illustrated embodiment, the dilator portion 42 includes an inner section 44 having an inner end 46 overlapped partially by an outer section 47 that has an outer end 48. The inner end 46 may be tapered to present a relatively smooth inner surface to enhance passage of the second chamber 24 and channel 26 through the entry opening 43 with minimal or preferably no blockage. The dilator portion 42 has a diameter that is adjustable from a smaller diameter to fit within the incision initially, preferably with minimal trauma and more preferably without trauma, and is expandable to a larger diameter to dilate the incision sufficiently to allow the implant in the breast implant assembly, which may be elastically deformed, to be inserted into the entry opening 43 of the incision dilator 36, then through the flexible, elastic portion 38, out through the expandable exit opening 40 and into the subject's body in at least an approximate desired position based on the particular breast reconstruction or breast augmentation procedure that is being performed.

The dilator portion 42 may be expanded and retained in an expanded, larger diameter position by virtue of the angled teeth 50 formed on the outer surface of the inner section 44 which interact with the like-angled teeth 52 formed on the inner surface of the outer section 47 of the dilator portion 42. In the orientation shown in FIG. 7, the dilator portion 42 expands to a larger diameter when the outer section 47 is moved in a clockwise direction by applying a suitable angular force to the butt end 48 of the outer section 47 while the inner section 44 and its end 46 are held in a stationary position. Once expanded, the angle of the teeth prevent the collapse of the dilator portion 42 from the larger diameter to the smaller diameter until the teeth 50, 52 are disengaged, such as by moving the inner section 44 radially inward and away from the outer section 47, which is done when the incision dilator 36 is to be removed from the incision.

While the expansion of the dilator portion 42 has been described by the relative clockwise movement of the outer section 47 compared to the stationary angular positioning of the inner section 44, if desired, the expansion can be accomplished by the relative counterclockwise movement of the inner section 44 compared to the stationary angular positioning of the outer section 47.

If desired and as preferable, there are indicia 54 and 56 on at least one of the outer peripheral surface 54 of the respective outer section 47 and the inner section 44 of the dilator portion 42, and/or indicia 60 on at least one of the front face 58 of the dilator portion 42. The indicia indicate the size of the opening 43 of the dilator portion 42 when in its smaller and larger diameter conditions. The indicia may be keyed to indicate the appropriate degree of expansion of the dilator portion based on the size of implants intended to pass through the entry opening 43. The indicia may be molded into the material used to form the incision dilator 36 or may be printed on the appropriate locations of the dilator portion as noted. The indicia 54, 56 and 60 may be lines of various lengths to be aligned with each other to indicate the size of the entry opening 43 or the size of the implant 10 to be inserted therein, or may be alphanumeric indicia, or color-coded indicia, or a combination of all of these types of indicia.

Once the incision is dilated, the second chamber 24 and at least a portion of the channel 26 are inserted into the entry opening 43 of the incision dilator 36 and at least the proximal (from the position inside the subject's body) end of the second chamber 24 preferably is pushed through the expandable exit opening 40 to place the proximal end of the second chamber 24 in at least an approximate location for the breast implant assembly within the subject's body. Then a distal portion of the first chamber 22 of the bag 20 containing the implant 10 is squeezed to deform the implant without damage and to move the implant from the first chamber 22 into the channel 26 within the incision dilator 36 and then into the second chamber 24 within and then through the exit opening 40 of the flexible, elastic portion 38 of the incision dilator 36 to the approximate desired location within the subject's body.

After the implant 10 within the second chamber 24 is in the approximate desired location, the second chamber 24 is closed at closure 34 as described above regarding FIG. 5, to encase the implant within the second chamber and within the subject's body. Then the bag 20 is cut at the channel 26 in the vicinity of the connection of the channel 26 to the second chamber 24 distally adjacent to the location where the second chamber 24 has been closed, such as denoted by dashed lines 32 in FIG. 5. The channel 26 and first chamber 22 cut away from the second chamber 24 are thereafter removed for disposal. As noted above, if desired, biodegradable glue also can be applied to the closure 34 after the excess portion of the bag 20 has been cut and removed, in lieu of or in addition to the application of any such glue prior to cutting and removing the excess portion of the bag 20.

The incision dilator 36 is then removed from the incision after having reduced the diameter of the dilator portion 42. If desired, removing the incision dilator 36 optionally may be done prior to the closing and cutting, but it is preferred that the incision dilator is kept in position during the closing and cutting to enhance the ease of these aspects of the method and procedure.

The implant encased within the second chamber is then positioned in the final desired location within the subject's body, followed by appropriate closure of the incision.

Another aspect of the invention is directed to a kit comprising at least a sterile bag according to any embodiment of the present invention, but preferably including both the bag and a matched sterile implant, and more preferably, the implant encased in the bag, as a breast implant assembly, which are preferably packaged in sterile packaging. The kit may also include a sterile incision dilator, such as, but not limited to the incision dilator 36 as described herein. Exemplary embodiments of such kits are shown in FIGS. 8 and 9, where like components of the two figures are identified by similar numerals, the identifying numerals of FIG. 9 being primed compared to the identifying numerals of FIG. 8.

The kit may include sterile packaging 62 for the first embodiment of the bag 12, shown as optionally containing the implant 10 as a preformed breast implant assembly in FIG. 8. FIG. 9 shows similar sterile packaging 62' for the second embodiment of the bag 20, shown as optionally containing the implant 10 in the first chamber 22 of the bag 20 as a preformed breast implant assembly. The bags in the kit are size matched to the implant supplied with the kit or separately. The kits are sterile.

The kits in the sterile packaging 62, 62' may have a container tray 64, 64' made of any suitable material, such as sterilizable synthetic polymeric plastic that is preferably transparent or translucent. The tray 64, 64' has a bottom 66, 66', and a conical side wall 68, 68', although the tray may have any number of walls if it is not circular in a horizontal cross-section. The tray is shown as having one continuous side wall 68, 68' that is circular in a horizontal cross-section for ease and clarity of description, rather than by way of any limitation. The wall preferably has an annular flange 70, 70' extending at about a right angle from the wall 68, 68'. The annular flange supports an cover 72, 72' that hermetically seals the packaging 62, 62', by the cover 72, 72' being sealed to the flange with any appropriate adhesive, heat sealing or the like, to assure sterility of the interior of the container tray and its contents, until the packaging is opened, such as by peeling portions 74, 74' of the cover that extend over the outer edge of the flange 70, 70' for ease of grasping. The cover 72, 72' preferably is a transparent or translucent synthetic polymeric plastic material, but can be made of a metal or other foil, if desired. The packaging 62, 62' is appropriately marked, such as on the container tray 64, 64' bottom 66, 66', side 68, 68' or cover 72, 72', and preferably all of the above, with appropriate indicia identifying the contents of the packaging 62, 62'.

The kits optionally contain instructions (not shown) for inserting the accompanying implant into the bag and/or for handling and surgically implanting the breast implant assembly in the subject. At the time of surgery, the kits are opened and the implant is inserted in the covering as described herein.

Figure 10:
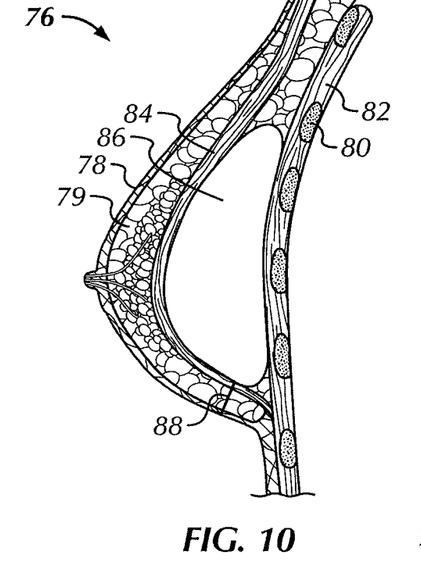
FIG. 10 is a vertical cross-sectional schematic representation of a human female breast schematically showing the approximate location of an inframammary incision through which a breast implant assembly of the present invention may be implanted into the female.
Figure 11:
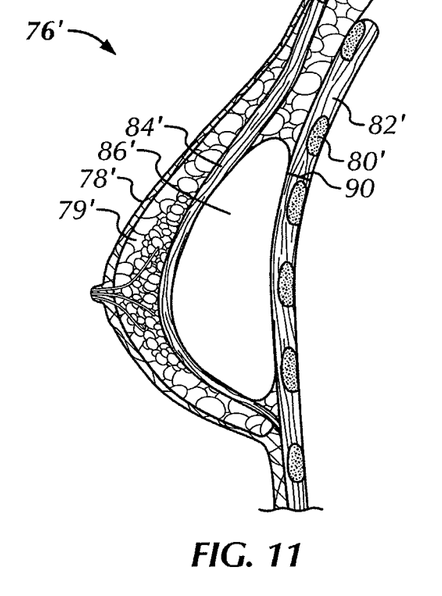
FIG. 11 is a vertical cross-sectional schematic representation of a human female breast schematically showing the approximate location of an axillary incision through which a breast implant assembly of the present invention may be implanted into the female.
Figure 12:
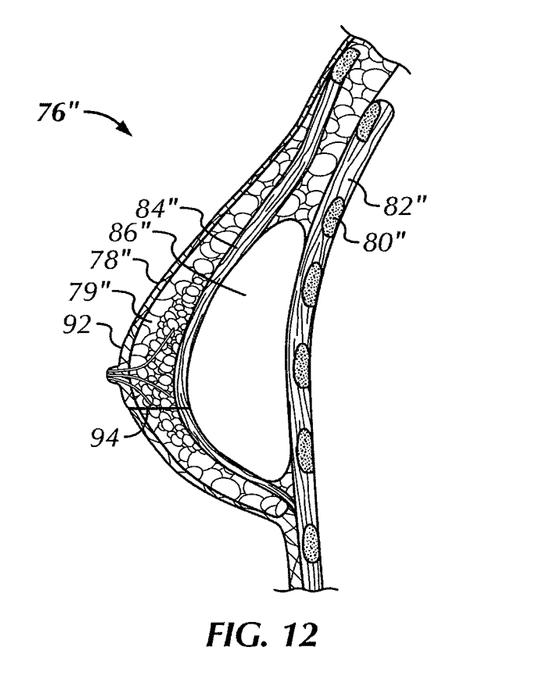
FIG. 12 is a vertical cross-sectional schematic representation of a human female breast schematically showing the approximate location of a periareolar incision through which a breast implant assembly of the present invention may be implanted into the female.

FIGS. 10-13 are schematic representations of a human female breast showing the approximate locations of incisions through which a breast implant 10 assembly of the breast implant encased within the bag 10 or 20 of the present invention may be implanted within the female according to the method of the present invention. The method may be performed with or without the use of the incision dilator 36 described above when the first embodiment of the breast implant assembly using the bag 12 is involved. FIGS. 10-13, and particularly FIGS. 10-12, have components that are identified by similar numerals, where the identifying numerals of the common components of FIG. 11 are primed compared to the identifying numerals of FIG. 10 and the identifying numerals of the common components of FIGS. 11 and 12 are double primed compared to the identifying numerals of FIG. 10.

With reference to FIGS. 10-13, breast 78, 78', 78" includes glandular tissue 79, 79', 79". The rib cage 80, 80' 80" is depicted. Musculature 82, 82', 82" and 84, 84' 84" are depicted as surrounding one exemplary location 86, 86', 86" for the implantation of the breast implant assembly of the present invention, where the location is exaggerated for purposes of clarity.

Figure 13:
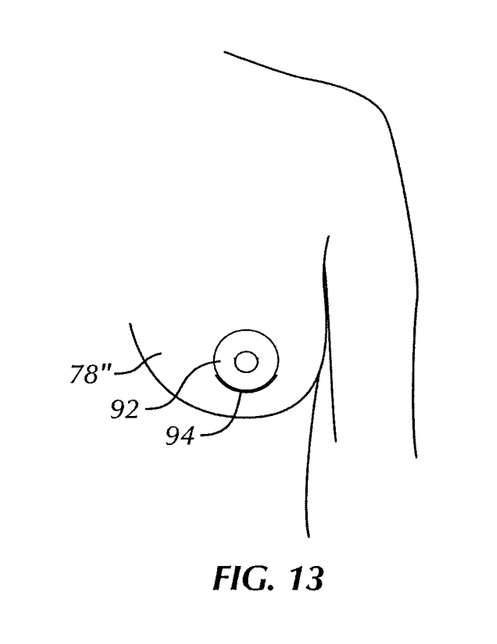
FIG. 13 is a front elevation view of a schematic representation of a partial human female torso showing the approximate location of the periareolar incision also shown in FIG. 12, through which a breast implant assembly of the present invention may be implanted into the female.

FIG. 10 schematically shows the approximate location of an inframammary incision through which a breast implant assembly of the present invention may be implanted into the female. FIG. 11 schematically shows the approximate location of an axillary incision through which a breast implant assembly of the present invention may be implanted into the female. FIGS. 12 and 13 schematically show the approximate location of a periareolar incision through which a breast implant assembly of the present invention may be implanted into the female.

All references, patents, patent applications or other documents cited are hereby incorporated by reference herein in their entirety.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A bag for retaining and sterile handling of a breast implant, the bag comprising first and second chambers each having a volume when expanded larger than the volume of the implant, the first chamber having a closable opening for insertion of the implant, the bag further having a channel connecting the chambers where the channel has a diameter smaller than either chamber but large enough to accommodate the implant when the implant is elastically deformed without damaging the implant such that the implant may be manually moved without directly touching the implant from the first chamber through the channel and into the second chamber without adversely affecting the implant, wherein the bag is made of a drug-eluting biodegradable material including at least one drug capable of at least reducing at least one of an infection and capsular contraction.

2. The bag of claim 1, wherein the at least one drug is selected from the group consisting of an antimicrobial agent, anti-inflammatory agent, anti-scarring agent, anti-neoplastic agent, a calcium channel blocker and leukotriene inhibitor.

3. The bag of claim 2, wherein the at least one drug is an antimicrobial agent.

4. The bag of claim 3, wherein the antimicrobial agent is selected from the group consisting of bacitracin, cephalexin and gentamicin, and mixtures thereof.

5. The bag of claim 2, wherein the at least one drug is a leukotriene inhibitor.

6. The bag of claim 5, wherein the leukotriene inhibitor is a leukotriene receptor antagonist selected from the group consisting of acitazanolast, iralukast, montelukast, pranlukast, verlukast, zafirlukast, and zileuton.

7. The bag of claim 1, wherein at least a portion of the bag has an outer surface selected from the group consisting of smooth, textured and crinkled.

8. A kit for use in handling and implanting a breast implant in a sterile manner, the kit comprising a sterile bag comprising first and second chambers each having a volume when expanded larger than the volume of the implant, the first chamber having a closable opening for insertion of the implant, the bag further having a channel connecting the chambers where the channel has a diameter smaller than either chamber but large enough to accommodate the implant when the implant is elastically deformed without damaging the implant such that the implant may be manually moved without directly touching the implant from the first chamber through the channel and into the second chamber without adversely affecting the implant, the bag being within openable sterile packaging, wherein the bag is made of a drug-eluting biodegradable material including at least one drug capable of at least reducing at least one of an infection and capsular contraction.

9. The kit of claim 8, wherein the at least one drug is selected from the group consisting of an antimicrobial agent, anti-inflammatory agent, anti-scarring agent, anti-neoplastic agent, a calcium channel blocker and leukotriene inhibitor.

10. The kit of claim 9, wherein the at least one drug is an antimicrobial agent.

11. The kit of claim 10, wherein the antimicrobial agent is selected from the group consisting of bacitracin, cephalexin and gentamicin, and mixtures thereof.

12. The kit of claim 9, wherein the at least one drug is a leukotriene inhibitor.

13. The kit of claim 12, wherein the leukotriene inhibitor is a leukotriene receptor antagonist selected from the group consisting of acitazanolast, iralukast, montelukast, pranlukast, verlukast, zafirlukast, and zileuton.

14. The kit of claim 8, wherein at least a portion of the bag has an outer surface selected from the group consisting of smooth, textured and crinkled.

15. A kit for use in handling and implanting a breast implant in a sterile manner, the kit comprising a sterile bag comprising first and second chambers each having a volume when expanded larger than the volume of the implant, the first chamber having a closable opening for insertion of the implant, the bag further having a channel connecting the chambers where the channel has a diameter smaller than either chamber but large enough to accommodate the implant when the implant is elastically deformed without damaging the implant such that the implant may be manually moved without directly touching the implant from the first chamber through the channel and into the second chamber without adversely affecting the implant, the bag being within openable sterile packaging, the kit further comprising a sterile breast implant, the breast implant being within openable sterile packaging, wherein the sterile packaging is selected from the same or different sterile packaging containing the bag.

16. A kit for use in handling and implanting a breast implant in a sterile manner, the kit comprising a sterile bag comprising first and second chambers each having a volume when expanded larger than the volume of the implant, the first chamber having a closable opening for insertion of the implant, the bag further having a channel connecting the chambers where the channel has a diameter smaller than either chamber but large enough to accommodate the implant when the implant is elastically deformed without damaging the implant such that the implant may be manually moved without directly touching the implant from the first chamber through the channel and into the second chamber without adversely affecting the implant, the bag being within openable sterile packaging, the kit further comprising a sterile breast implant encased in a sterile manner within the first chamber of the bag.

* * * * *